(12) United States Patent
Morita et al.

(10) Patent No.: US 8,068,702 B2
(45) Date of Patent: Nov. 29, 2011

(54) SYSTEM, METHOD AND COMPUTER INSTRUCTIONS FOR AIDING IMAGE ANALYSIS

(75) Inventors: Mark M. Morita, Arlington Heights, IL (US); Prakash Mahesh, Schaumburg, IL (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 12/770,282

(22) Filed: Apr. 29, 2010

(65) Prior Publication Data

US 2010/0215241 A1 Aug. 26, 2010

Related U.S. Application Data

(63) Continuation of application No. 11/443,543, filed on May 30, 2006, now abandoned.

(51) Int. Cl.
*G06K 9/60* (2006.01)
*G06K 9/66* (2006.01)
*G06K 9/00* (2006.01)

(52) U.S. Cl. ............. 382/305; 382/128; 382/190; 706/6

(58) Field of Classification Search .......... 382/128–132, 382/209, 305; 322/1; 428/922; 405/2, 3; 707/3; 706/3, 6
See application file for complete search history.

(56) References Cited

U.S. PATENT DOCUMENTS

| | | | | |
|---|---|---|---|---|
| 5,010,581 A * | 4/1991 | Kanno | | 382/305 |
| 6,016,487 A | 1/2000 | Rioux et al. | | |
| 6,173,275 B1 * | 1/2001 | Caid et al. | | 706/14 |
| 6,173,287 B1 * | 1/2001 | Eberman et al. | | 715/232 |
| 6,292,577 B1 * | 9/2001 | Takahashi | | 382/128 |
| 6,434,569 B1 * | 8/2002 | Toshimitsu et al. | | 1/1 |
| 6,453,059 B2 * | 9/2002 | Ogawa | | 382/132 |
| 6,859,288 B1 * | 2/2005 | Brackett et al. | | 358/1.15 |
| 7,043,474 B2 * | 5/2006 | Mojsilovic et al. | | 1/1 |
| 7,120,644 B1 * | 10/2006 | Canessa et al. | | 1/1 |
| 7,366,992 B2 * | 4/2008 | Thomas, III | | 715/764 |
| 7,457,656 B2 * | 11/2008 | Judd et al. | | 600/407 |
| 7,885,440 B2 * | 2/2011 | Fram et al. | | 382/128 |
| 2002/0138301 A1 * | 9/2002 | Karras et al. | | 705/2 |
| 2003/0195883 A1 * | 10/2003 | Mojsilovic et al. | | 707/6 |
| 2007/0280561 A1 | 12/2007 | Morita et al. | | |

OTHER PUBLICATIONS

Lehmann et al, The IRMA code for unique classification of medical images, In Proceedings SPIE (2003), pp. 109-117.*
Deselaers, T., Weyand, T., Keysers, D., Macherey, W., Ney, H.: Fire in imageclef 2005: Combining content-based image retrieval with textual information retrieval. Image Cross Language Evaluation Forum (2005).*

(Continued)

*Primary Examiner* — Gregory M Desire
*Assistant Examiner* — Andrae S Allison
(74) *Attorney, Agent, or Firm* — Hanley, Flight & Zimmerman, LLC

(57) ABSTRACT

Certain embodiments of the present invention provide a system, method and computer instructions for aiding analysis of an image used in a medical examination. For example, in an embodiment, an image analysis system used in a medical examination comprises: an input module configured to input an image; a search module configured to locate information regarding an image that is similar to the input image; and an output module configured to output a link to the located information, wherein the located information is displayed when the link is used. For example, in an embodiment, an image analysis system used in a medical examination further comprises a communication module, wherein the communication module is configured to output the input image and the located information, and wherein the communication module is configured to receive a responsive communication.

18 Claims, 3 Drawing Sheets

OTHER PUBLICATIONS

United States Patent and Trademark, "Final Office Action" issued in connection with U.S. Appl. No. 11/443,543, mailed Dec. 29, 2009 (18 pages).

United States Patent and Trademark, "Non-Final Office Action" issued in connection with U.S. Appl. No. 11/443,543, mailed Jun. 22, 2009 (14 pages).

Lehmann et al, "The IRMA Code for Unique Classification of Medical Images," In Proceedings SPIE (2003), Aug. 3, 2003, pp. 440-451, San Diego, CA, USA (12 pages).

Deselaers, et al., "FIRE in Imageclef 2005: Combining Content-based Image Retrieval with Textual Information Retrieval," Image Cross Language Evaluation Forum, 2005 (9 pages).

* cited by examiner

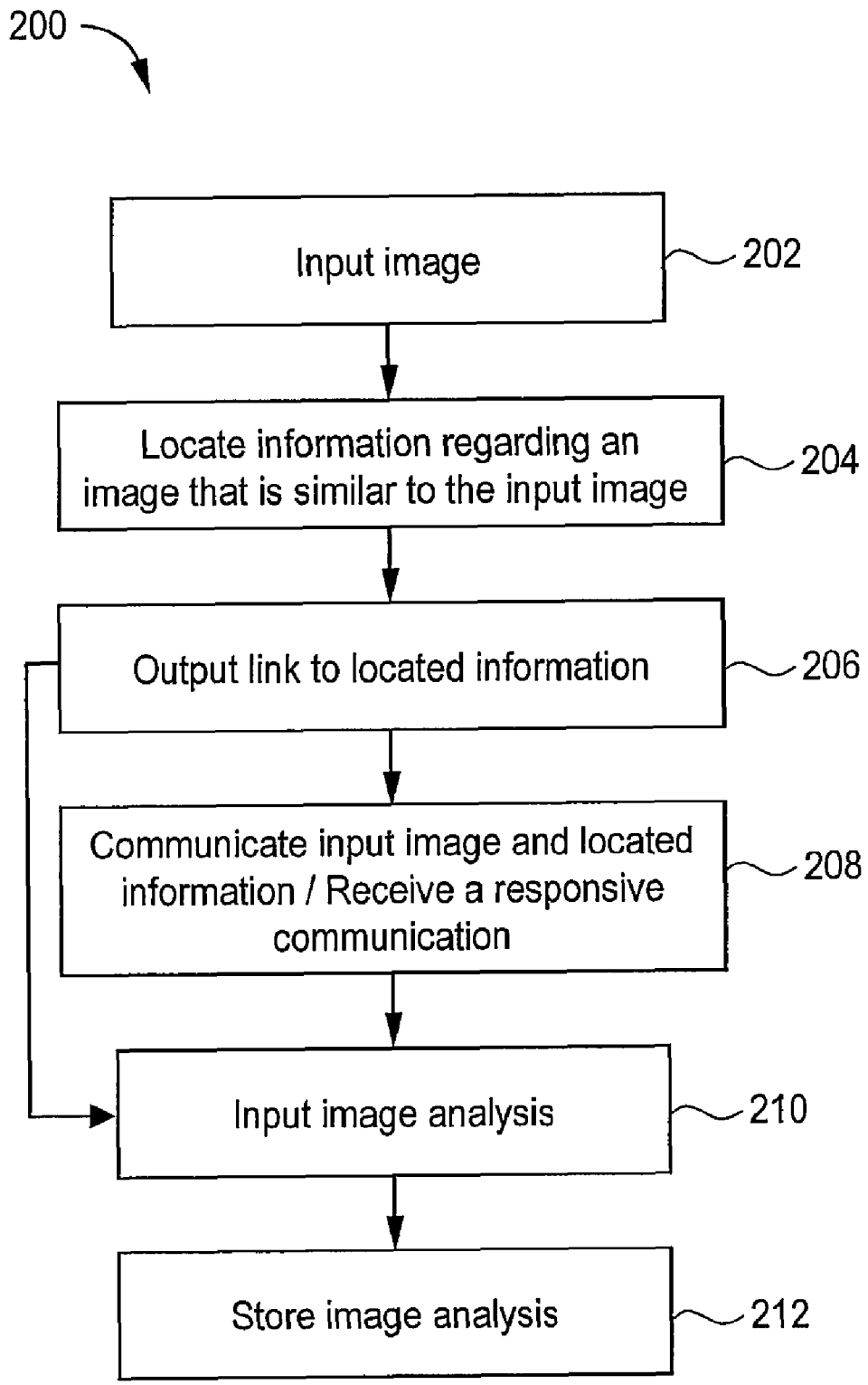

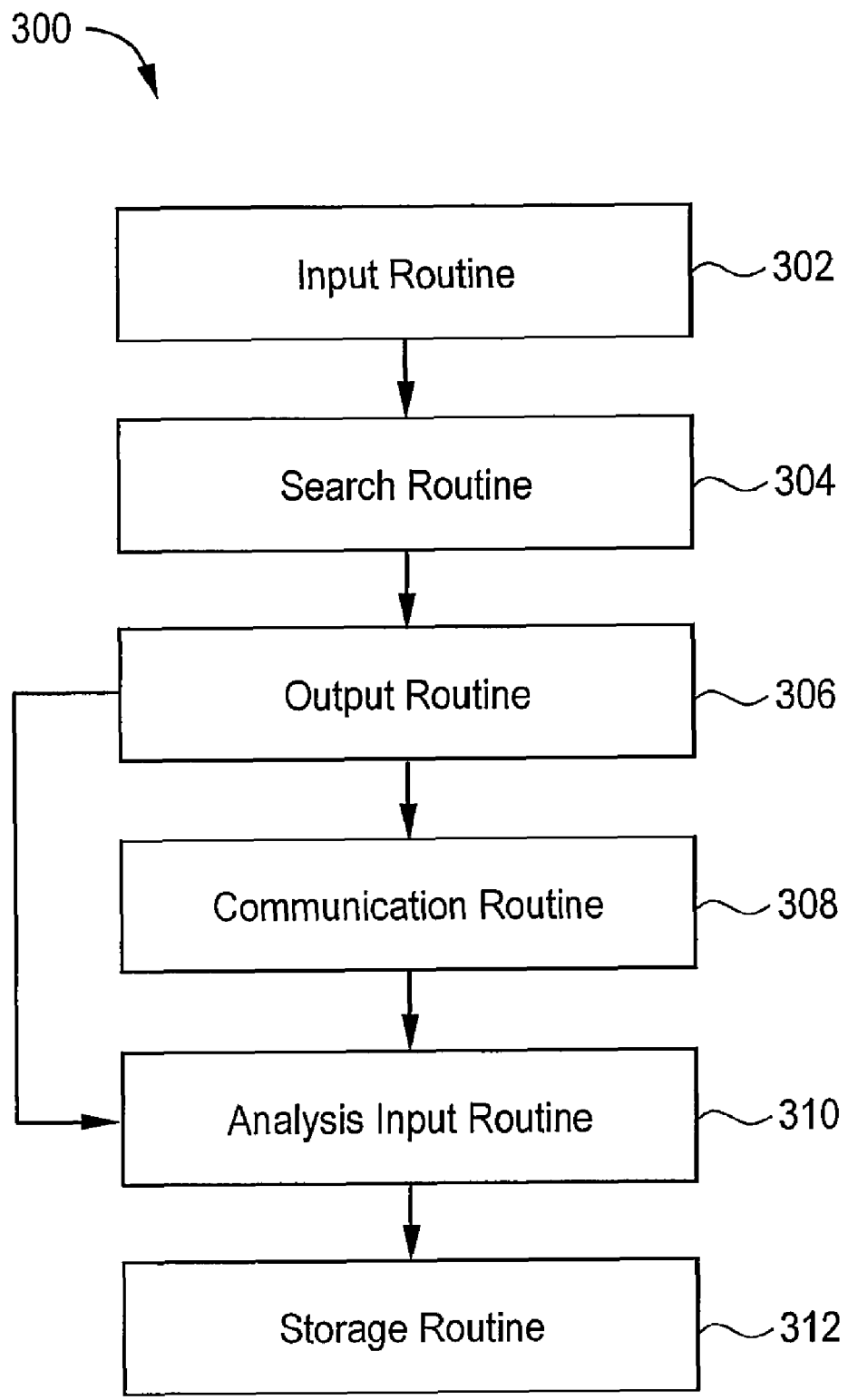

SYSTEM, METHOD AND COMPUTER INSTRUCTIONS FOR AIDING IMAGE ANALYSIS

CROSS-REFERENCE TO RELATED APPLICATIONS

The present application is a continuation of and claims the benefit of priority to U.S. patent application Ser. No. 11/443,543, filed on May 30, 2006, now abandoned, entitled "System, Method And Computer Instructions For Aiding Image Analysis", which is herein incorporated by reference in its entirety.

BACKGROUND OF THE INVENTION

The present invention generally relates to systems, methods and computer instructions for aiding image analysis. More particularly, the present invention relates to systems, methods and computer instructions for aiding image analysis by providing a link to information regarding an image that is similar to an image that is being analyzed.

Images can be used to aid in the monitoring and/or diagnosis of ailments. Such images are created using imaging systems. Two types of imaging techniques utilized by imaging systems are Computed Tomography (CT) imaging and/or Magnetic Resonance (MR) imaging, for example. Images collected using an imaging system are referred to collectively as an imaging study. Once an imaging study is completed, the images therein can be displayed on a workstation, such as a Picture Arching and Communicating System (PACS) workstation, for example.

When an image is presented for review, a certain portion of the image can be considered interesting because, for example, that portion of the image could indicate abnormality. Abnormality in an image could indicate a certain disease, also known as, pathology. Thus, once abnormality is discovered, it is desirable to identify and diagnose the pathology that could be causing the abnormality.

People that review medical images, such as radiologists, for example, usually rely on past training and/or individual research in order to identify and diagnose pathology. Sometimes pathology is readily identified and diagnosed. However, when there is difficulty identifying and diagnosing unfamiliar pathology, time can be spent manually researching in order to identify and diagnose pathology. Further, mistakes can be made when identifying and diagnosing unfamiliar pathology.

There are systems that incorporate what is known as Computer Aided Diagnosis (CAD), which can aid in the identification of areas of interest in an image and mark such areas so that a user that is reviewing the image is alerted to the area. Further, systems that incorporate CAD can suggest pathology based on a comparison of the image to previously analyzed images. However, systems that incorporate CAD can provide false positives, that is, systems that incorporate CAD can falsely mark an area of an image as an area of interest when there is no pathology in that area of the image. Thus, although systems that incorporate CAD may be effective when pathology is readily identified and diagnosed, if there is difficulty identifying and diagnosing unfamiliar pathology, a person reviewing an image can still spend time manually researching in order to identify and diagnose pathology.

Thus, there is a need for a system, method and computer instructions for aiding image analysis that provides improved and/or streamlined identification and diagnosis of pathology in an image used in a medical examination.

BRIEF SUMMARY OF THE INVENTION

Certain embodiments of the present invention provide a system, method and computer instructions for aiding analysis of an image used in a medical examination. For example, in an embodiment, an image analysis system used in a medical examination comprises: an input module configured to input an image; a search module configured to locate information regarding an image that is similar to the input image; and an output module configured to output a link to the located information, wherein the located information is displayed when the link is used. For example, in an embodiment, an image analysis system used in a medical examination further comprises a communication module, wherein the communication module is configured to output the input image and the located information, and wherein the communication module is configured to receive a responsive communication.

For example, in an embodiment, a method for aiding analysis of an image used in a medical examination comprises: inputting an image; locating information regarding an image that is similar to the input image; and outputting a link to the located information, wherein the located information is displayed when the link is used. For example, in an embodiment, a method for aiding analysis of an image used in a medical examination further comprises: outputting the input image and located information; and receiving a responsive communication.

For example, in an embodiment, a computer-readable storage medium includes a set of computer instructions for aiding analysis of an image used in a medical examination, and the set of instructions comprises: an input routine that allows an image to be input; a search routine that allows information regarding an image that is similar to the input image to be located; and an output routine that allows a link to the located information to be output, wherein the located information is displayed when the link is used. For example, in an embodiment, a computer-readable storage medium includes a set of computer instructions for aiding analysis of an image used in a medical examination, and the set of instructions further comprises a communication routine, wherein the communication routine allows the input image and the located information to be output, and wherein the communication routine allows a responsive communication to be received.

BRIEF DESCRIPTION OF THE DRAWINGS

FIG. 2 illustrates a method for aiding analysis of an image used in accordance with an embodiment of the present invention.

FIG. 3 illustrates a set of computer instructions for aiding analysis of an image used in accordance with an embodiment of the present invention.

Figure 1:
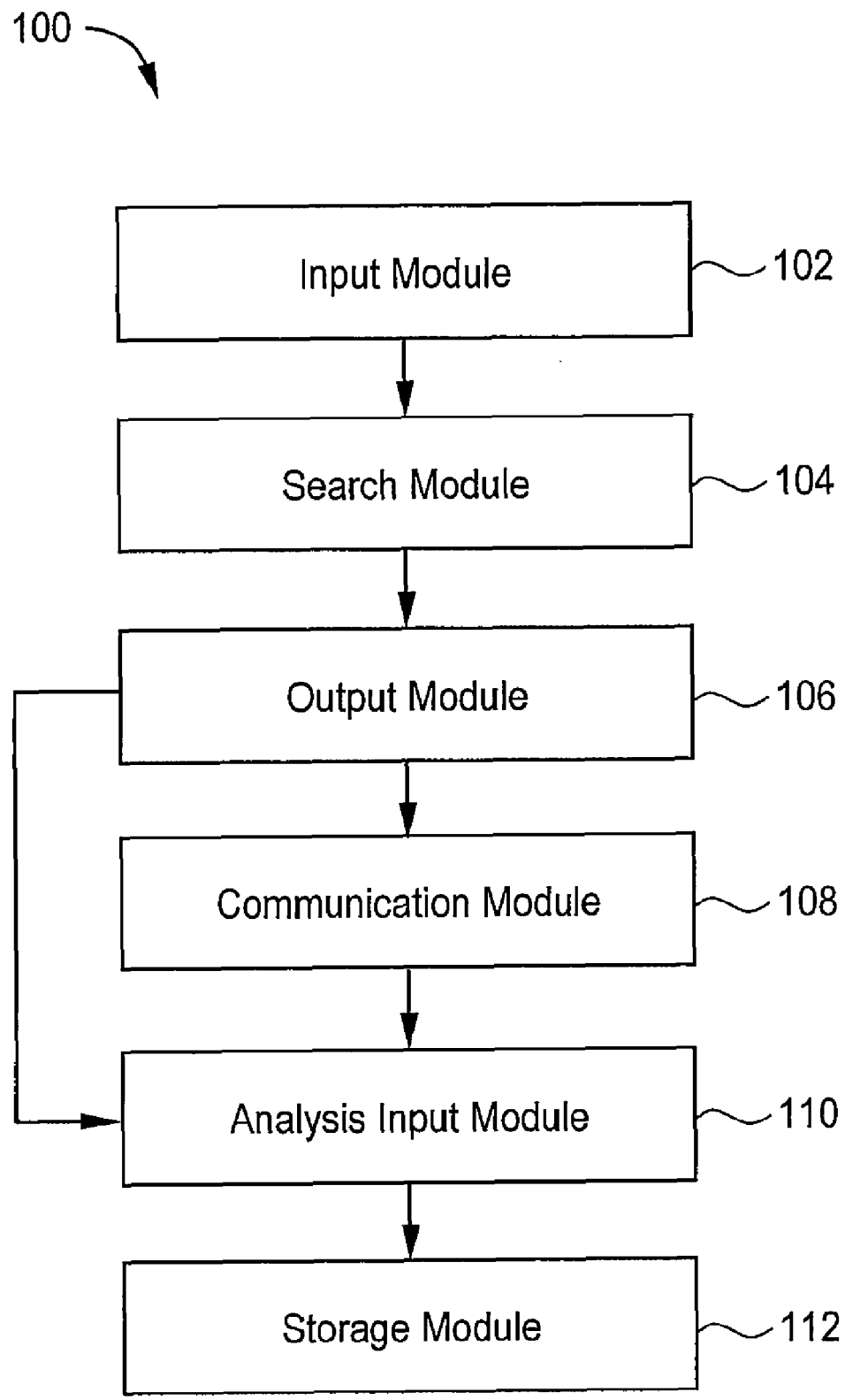
FIG. 1 illustrates an image analysis system used in accordance with an embodiment of the present invention.

The foregoing summary, as well as the following detailed description of embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF CERTAIN EMBODIMENTS

FIG. 1 illustrates an image analysis system 100 used in accordance with an embodiment of the present invention. The system 100 in FIG. 1 includes an input module 102, a search module 104, an output module 106, a communication module 108, an analysis input module 110 and a storage module 112.

In the system 100, the input module 102 is configured to input an image. The input module 102 can be configured to input many types of images. For example, in certain embodiments, the input module 102 can be configured to input an image created using Computed Tomography (CT) imaging and/or Magnetic Resonance (MR) imaging. Other ways to configure the input module 102 to input other types of images may exist, as known to those skilled in the art.

In the system 100, the input module 102 can be configured to input an image in many ways. For example, in certain embodiments, the input module 102 can be configured to input an image that is a selected portion of an image. In an example, a selected portion of an image can be a portion of the image that is suspected of showing pathology. In an example, a portion of an image that is suspected of showing pathology can be the entire image. In certain embodiments, the input module 102 can be configured to input an image that is a portion of an image that is selected by a user of an image review workstation. In an example, an image review workstation can be a Picture Arching and Communicating System (PACS) workstation. In an example, a user of an image review workstation can include a radiologist, a technician or a cardiologist. In certain embodiments, the input module 102 can be configured to input an image that is a portion of an image that is selected by a system that incorporates Computer Aided Diagnosis (CAD). Other ways to configure the input module 102 to input images may exist, as known to those skilled in the art.

In the system 100, the input module 102 can be configured to input image information. The input module 102 can be configured to input many types of image information. For example, in certain embodiments, the input module 102 can be configured to input image information that includes: information regarding the type of imaging system that created the image, also known as, modality information; information regarding the body part that the image depicts; information regarding the contrast agent; and/or other Digital Imaging and Communications in Medicine (DICOM) header information. Other ways to configure the input module 102 to allow other types of image information to be input may exist, as known to those skilled in the art.

In the system 100, the input module 102 can be configured to input image information in many ways. For example, in certain embodiments, the input module 102 can be configured to input image information from: an imaging system; a database that is part of a Radiologist Information System (RIS); a database that is part of a Hospital Information System (HIS); a database that is accessible via the Internet; a local database; and/or any information source that is in networked communication with the input module 102. Other ways to configure the input module 102 to input image information may exist, as known to those skilled in the art.

In the system 100, the search module 104 is configured to locate information regarding an image that is similar to the input image. The search module 104 can be configured to locate information regarding an image that is similar to the input image in many ways. For example, in certain embodiments, the search module 104 can be configured to use an image recognition algorithm to identify images that are similar to the input image. For example, in certain embodiments, the search module 104 can be configured to restrict a search for an image that is similar to the input image based on information regarding the input image. In such embodiments, the search module 104 can be configured to restrict a search for an image that is similar to the input image based on modality information, body part information, contrast agent information and/or other DICOM header information, for example. Other ways to configure the search module 104 to locate information regarding an image that is similar to the input image may exist, as known to those skilled in the art.

In the system 100, the search module 104 can be configured to locate information regarding an image that is similar to the input image in many places. For example, in certain embodiments, the search module 104 can be configured to locate information that is accessible on a HIS, a RIS and/or the Internet. Other ways to configure the search module 104 to locate information in other places may exist, as known to those skilled in the art.

In the system 100, the search module 104 can be configured to locate many types of information. For example, in certain embodiments, the search module 104 can be configured to locate a previous image analysis, an article, a report and/or a web page that includes an image similar to the input image. In an example, a previous image analysis can include an image(s) and associated annotation, such as text and/or audio that include analysis and/or a conclusion/diagnosis. Other ways to configure the search module 104 to locate other types of information may exist, as known to those skilled in the art.

In the system 100, the output module 106 is configured to output a link to located information. The output module 106 can be configured to output a link to located information in many ways. For example, in an embodiment, the output module 106 can be configured to output a link as a visual display. In such an embodiment, the output module 106 can be configured to output a link to an image review workstation, such as a PACS workstation, for example. In such an embodiment, the link can link to information that is accessible on a HIS, a RIS and/or the Internet, and the information can be displayed when the link is used, for example. Other ways to configure the output module 106 to output a link to located information may exist, as known to those skilled in the art.

In the system 100, the communication module 108 is configured to output an input image and located information and receive a responsive communication. The communication module 108 can be configured to output an input image and located information and receive a responsive communication in many ways. For example, in an embodiment, the communication module 108 can be configured to output an input image and located information and receive a responsive communication via a collaboration system that allows patrons of the collaboration system to review the image and located information and provide a response. For example, in an embodiment, the communication module 108 can be configured to output an input image and located information and receive a responsive communication via a collaboration system that uses an instant messenger-like service or chat-room-like format to circulate an input image and located information and allow for a response to be provided, for example. Other ways to configure the communication module 108 to output the input image and the located information and receive a responsive communication may exist, as known to those skilled in the art.

In the system 100, the analysis input module 110 is configured to input analysis information. The analysis input module 110 can be configured to input analysis information in many ways. For example, in an embodiment, the analysis input module 110 can be configured to input analysis information from an image review workstation, such as a PACS workstation, for example. Other ways to configure the analysis input module 110 to input analysis information may exist, as known to those skilled in the art.

In the system 100, the analysis input module 110 can be configured to input many types of analysis information. For example, in an embodiment, the analysis input module 110 can be configured to input analysis information as an image(s), text and/or audio. For example, in an embodiment, analysis information can include: the input image as input and/or with markings on the image; other images that were included with the located information; typed or written text created by the user of the image review station; text that was included with the located information; audio created by the user of the image review station; and/or audio that was included with the located information. Other ways to configure the analysis input module 110 to input other types of analysis information may exist, as known to those skilled in the art.

In the system 100, the storage module 112 is configured to store analysis information. The storage module 112 can be configured to store analysis information in many places. For example, in an embodiment, the storage module 112 can be configured to store analysis information in: a database that is part of a RIS; a database that is part of a HIS; a database that is accessible via the Internet; a local database; and/or any database that is in networked communication with the storage module 112. Other ways to configure the storage module 112 to store analysis information in other places may exist, as known to those skilled in the art.

The modules of the system 100 can be implemented in many ways. For example, the modules can be implemented in hardware and/or software. The modules can be implemented separately and/or integrated in various combinations. Other desirable ways to implement the modules of the system 100 may exist, as known to those skilled in the art.

The system 100 can also be implemented in many ways. For example, the system 100 can be integrated with existing applications that run on a Microsoft® platform and/or other platforms as an add-on product. In one implementation, the system 100 can be integrated with a workstation(s) that is connected to a HIS and/or a RIS, such as a PACS workstation, for example. Other desirable ways to implement the system 100 may exist, as known to those skilled in the art.

In operation, an embodiment of the system 100 can be implemented in connection with a HIS and/or a RIS, for example. In such an embodiment, the input module 102 can be configured to input an image from an image review station, such as a PACS workstation, for example. For example, an image of a spine can be input into the image review workstation. The user of the image review workstation can then identify an area of the image that may contain an abnormality. For example, the user of the image review workstation could identify an area of the image that contains a separation in the spine. The image could then be cropped to create a new image that is focused on the spine separation. The new image can be input into the input module 102. The search module 104 could then search images accessible on a HIS, a RIS and/or the Internet to locate an image(s) that is similar to the input image. In an embodiment, image information, such as, modality information, body part information, contrast agent information and/or other DICOM header information, for example, can also be input into the input module 102, and the search module 104 can restrict searches for images based on the image information. When an image that is similar to the input image is found, a link to the information regarding the located image can be output via the output module 106. For example, a link to a previous image analysis, an article, a report and/or a web page can be output as a visual display to an image review workstation, such as a PACS workstation, for example. In this example, where the input image includes a spine separation, links that could be output include: a link to a previous image analysis where a spine separation was diagnosed as a fracture; a link to a previous image analysis where a spine separation was diagnosed as a hairline fracture; a link to a previous image analysis where a spine separation was diagnosed as a rupture; a link to a report/article regarding Orthopedic Guidelines; a link to the web page ehealth.com; a link to a lab report for Calcium; a link to prior CT images; and/or a link to prior MR images, for example. After the links are output, a user of the image review station can review the information by selecting the links. If the user of the image review station is not ready to make a diagnosis, the communication module 108 can output the input image and the located information and receive a responsive communication via a collaboration system that uses an instant messenger-like service or chat-room-like format to circulate an input image and located information and allow for a response to be provided, for example. When the user of the image review station is ready to make a diagnosis, the user can input image analysis information into the analysis input module 110. For example, the user can input image analysis or annotation information that includes an image(s), text and/or audio into the analysis input module 110. For example, the user can input: the input image as input and/or with markings on the image; other images that were included with the located information; typed or written text created by the user of the image review station; text that was included with the located information; audio created by the user of the image review station; and/or audio that was included with the located information. Once the analysis information has been input, the storage module 112 can store the analysis information. For example, the storage module 112 can store the analysis information in: a database that is part of a RIS; a database that is part of a HIS; a database that is accessible via the Internet; a local database; and/or any database that is in networked communication with the storage module 112.

In operation, another embodiment of the system 100 can be implemented in connection with a HIS and/or a RIS, for example. In such an embodiment, the input module 102 can be configured to input an image from a system that incorporates CAD. For example, an image of a kidney can be input into a system that incorporates CAD. The system that incorporates CAD can then identify an area of the image that may contain an abnormality. For example, the system that incorporates CAD could identify an area of the image that contains a mass on the kidney. The image could then be cropped to create a new image that is focused on the kidney mass. The new image can be input into the input module 102. The search module 104 could then search images accessible on a HIS, a RIS and/or the Internet to locate an image(s) that is similar to the input image. In an embodiment, image information, such as, modality information, body part information, contrast agent information and/or other DICOM header information, for example, can also be input into the input module 102, and the search module 104 can restrict searches for images based on the image information. When an image that is similar to the input image is found, a link to the information regarding the located image can be output via the output module 106. For example, a link to a previous image analysis, an article, a report and/or a web page can be output as a visual display to an image review workstation, such as a PACS workstation, for example. In this example, where the input image includes a kidney mass, links that could be output include: a link to a previous image analysis where a mass on a kidney was diagnosed as a tumor; a link to a previous image analysis where a mass on a kidney was diagnosed as a cyst; a link to a previous image analysis where a mass on a kidney was diagnosed as a malignant tumor; a link to a report/article regarding Sloan Kettering Guidelines; a link to a report/article regarding the American Cancer Society; a link to the web page mayo.com; a link to a lab report for Creatinine; a link to a lab report for Hematocrit; a link to a lab report for Gleason's Score; and/or a link to a lab report for PH Value, for example. After the links are output, a user of the image review station can review the information by selecting the links. Then the user can communicate with patrons of a collaboration system via the communication module 108 and/or input analysis information via the analysis input module 110 as described above with regard to the spine example. Once analysis information is input, the storage module 112 can store the analysis information as described above with regard to the spine example.

In operation, another embodiment of the system 100 can be implemented in connection with a HIS and/or a RIS, for example. In such an embodiment, the input module 102 can be configured to input an image from an image review station, such as a PACS workstation, for example, after the image has already been analyzed by a system that incorporates CAD. For example, an image of a breast can be input into the image review workstation from a system that incorporates CAD. The user of the image review workstation can review the image and decide whether the portion of the image that was identified by CAD as containing an abnormality, such as a lump, is the portion of the image that should be analyzed. If the user of the image review workstation agrees with the CAD analysis, the image could then be cropped to create a new image that is focused on the lump. If the user of the image review workstation does not agree with the CAD analysis, the user of the image review station can select a different portion of the image that the user believes contains an abnormality, such as a lump, and the image can be cropped to create a new image that is focused on the abnormality. The new image can be input into the input module 102. The search module 104 could then search images accessible on a HIS, a RIS and/or the Internet to locate an image(s) that is similar to the input image. In an embodiment, image information, such as, modality information, body part information, contrast agent information and/or other DICOM header information, for example, can also be input into the input module 102, and the search module 104 can restrict searches for images based on the image information. When an image that is similar to the input image is found, a link to the information regarding the located image can be output via the output module 106. For example, a link to a previous image analysis, an article, a report and/or a web page can be output as a visual display to an image review workstation, such as a PACS workstation, for example. In this example, where the input image includes a lump in a breast, links that could be output include: a link to a previous image analysis where a lump in a breast was diagnosed as a cyst; a link to a previous image analysis where a lump in a breast was diagnosed as a fibroid cyst; a link to a previous image analysis where a lump in a breast was diagnosed as scar tissue; a link to a report/article regarding Cysts; a link to a report/article regarding the JAMA; a link to the web page bCancer.com; and/or a link to the web page eMed.com, for example. After the links are output, a user of the image review station can review the information by selecting the links. Then the user can communicate with patrons of a collaboration system via the communication module 108 and/or input analysis information via the analysis input module 110 as described above with regard to the spine example. Once analysis information is input, the storage module 112 can store the analysis information as described above with regard to the spine example.

FIG. 2 illustrates a method for aiding analysis of an image 200 used in accordance with an embodiment of the present invention. At 202, an image is input. For example, an image can be a portion of an image that a user of an image review workstation, such as a PACS workstation, for example, and/or a system that incorporates CAD has identified as possibly including pathology. At 204, information regarding an image that is similar to the input image is located. For example, information can be located that is accessible on a HIS, a RIS and/or the Internet. Also, in an example, locating information can include using an image recognition algorithm to identify previously analyzed images that are similar to the input image. Also, in an example, image information, such as, modality information, body part information, contrast agent information and/or other DICOM header information, for example, can also be input, and used as a basis for restricting a search for information regarding an image that is similar to the input image. Also, in an example, located information can include a previous image analysis, an article, a report and/or a web page. At 206, a link to the located information is output. For example, a link to the located information can be output as a visual display to an image review station, such as a PACS workstation, for example. At 208, the input image and the located information are output and a responsive communication is received. For example, the input image and the located information can be output and a responsive communication can be received via a collaboration system that uses an instant messenger-like service or chat-room-like format to circulate information and allow for a response to be provided, for example. At 210, an analysis of the input image is input. For example, an analysis of the input image can be input as an image(s), text and/or audio at an image review workstation, such as a PACS workstation, for example. At 212, the analysis of the input image is stored. For example, the analysis of the input image can be stored in: a database that is part of a RIS; a database that is part of a HIS; a database that is accessible via the Internet; a local database; and/or any database that is in networked communication.

Due to the many types of pathology that exist, identifying and diagnosing pathology shown in an image used in a medical examination can be difficult and time consuming. Applying the method 200, as described above and/or in light of the description of FIG. 1, may provide improved and/or streamlined identification and diagnosis of pathology in images used in a medical examination.

FIG. 3 illustrates a set of computer instructions for aiding analysis of an image 300 used in accordance with an embodiment of the present invention. The set of computer instructions 300 in FIG. 3 includes an input routine 302, which allows an image to be input; a search routine 304, which allows information regarding an image that is similar to the input image to be located; an output routine 306, which allows a link to the located information to be output; a communication routine 308, which allows an input image and the located information to be output and a responsive communication to be received; an analysis input routine 310, which allows image analysis information to be input; and a storage routine 312, which allows image analysis information to be stored.

In certain embodiments, the input routine 302, the search routine 304, the output routine 306, the communication routine 308, the analysis input routine 310 and the storage routine 312 may be implemented and/or may perform functions similar to the input module 102, the search module 104, the output module 106, the communication module 308, the analysis input module 310 and the storage module 312, respectively, as described above in relation to FIG. 1.

While the invention has been described with reference to embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiments disclosed, but that the invention will include all embodiments falling within the scope of the appended claims.

The invention claimed is:

1. An image analysis system used in a medical examination comprising:
   a processor coupled to a memory, wherein the processor is programmed to implement the image analysis system comprising:
   an input module to accept an input including a first image having a first associated image analysis and first associated image header information;
   a search module to identify a second image that is similar to the first image based at least in part on a comparison of the first associated image analysis to a second image analysis associated with the second image and a comparison of the first image to the second image, the search module to restrict a search to identify the second image based on the first associated image header information; and
   an output module to output at least a link to the second image having second associated image analysis, wherein the second image having second associated image analysis is displayed when the link is used,
   wherein the first associated image analysis and the second associated image analysis comprise first and second image annotations associated with the first image and the second image, respectively, and wherein a user selects the first image annotation on the first image to initiate an automated search using the search module to identify the second image based on a comparison of the first image annotation and the second image annotation.

2. The system of claim 1, wherein at least one of the first associated image analysis and the second associated image analysis further includes an article, a report and a web page associated with at least one of the first image and the second image.

3. The system of claim 1, wherein the search module is to use an image recognition algorithm to identify the second image that is similar to the first image.

4. The system of claim 1, wherein the first associated image header information includes at least one of: modality information, body part information and contrast agent information, and wherein the search module is to restrict a search based on at least one of: modality information, body part information and contrast agent information.

5. The system of claim 1, further comprising a communication module, wherein the communication module is to output the first image and the second image and associated image analysis, and wherein the communication module is to receive a responsive communication for collaboration regarding the first image.

6. The system of claim 1, wherein the output module is to output the link as a visual display to a Picture Arching and Communicating System workstation.

7. A computer-implemented method for aiding analysis of an image used in a medical examination comprising:
   accepting, using a computer, an input including a first image having a first associated image analysis and first associated image header information;
   automatically searching a data storage, using the computer, to identify a second image that is similar to the first image based at least in part on a comparison of the first associated image analysis to a second image analysis associated with the second image and a comparison of the first image to the second image, the search module to restrict a search to identify the second image based on the first associated image header information; and
   outputting, via an interface at the computer, at least a link to the second image having second associated image analysis, wherein the second image having second associated image analysis is displayed when the link is used,
   wherein the first associated image analysis and the second associated image analysis comprise first and second image annotations associated with the first image and the second image, respectively, and wherein a user selects the first image annotation on the first image to initiate an automated search using the search module to identify the second image based on a comparison of the first image annotation and the second image annotation.

8. The computer-implemented method of claim 7, wherein at least one of the first associated image analysis and the second associated image analysis further includes an article, a report and a web page associated with at least one of the first image and the second image.

9. The computer-implemented method of claim 7, wherein said searching includes using an image recognition algorithm to identify an image that is similar to the input image.

10. The computer-implemented method of claim 7, wherein the first associated image header information includes at least one of: modality information, body part information and contrast agent information, and wherein said searching further comprises restricting the search based on at least one of: modality information, body part information and contrast agent information.

11. The computer-implemented method of claim 7, further comprising:
   outputting, using the computer, the first image and the second image and associated image analysis; and
   receiving a responsive communication to facilitate collaboration regarding the first image.

12. The computer-implemented method of claim 7, wherein the link is output as a visual display to a Picture Arching and Communicating System workstation.

13. A non-transitory computer-readable storage medium including a set of computer instructions for aiding analysis of an image used in a medical examination, the set of instructions comprising:
   an input routine to accept an input including a first image having a first associated image analysis and first associated image header information;
   a search routine to identify a second image that is similar to the first image based at least in part on a comparison of the first associated image analysis to a second image analysis associated with the second image and a comparison of the first image to the second image, the search module to restrict a search to identify the second image based on the first associated image header information; and
   an output routine to output at least a link to the second image having second associated image analysis, wherein the second image having second associated image analysis is displayed when the link is used, wherein the first associated image analysis and the second associated image analysis comprise first and second image annotations associated with the first image and the second image, respectively, and wherein a user selects the first image annotation on the first image to initiate an automated search using the search module to identify the second image based on a comparison of the first image annotation and the second image annotation.

14. The non-transitory computer-readable storage medium of claim 13, wherein at least one of the first associated image analysis and the second associated image analysis further includes an article, a report and a web page associated with at least one of the first image and the second image.

15. The non-transitory computer-readable storage medium of claim 13, wherein the search routine is to use an image recognition algorithm to identify the second image that is similar to the first image.

16. The non-transitory computer-readable storage medium of claim 13, wherein the first associated image header information includes at least one of: modality information, body part information and contrast agent information, and wherein the search module is to restrict a search based on at least one of: modality information, body part information and contrast agent information.

17. The non-transitory computer-readable storage medium of claim 13, further comprising a communication routine, wherein the communication routine is to output the first image and the second image and the associated image analysis, and wherein the communication routine is to receive a responsive communication for collaboration regarding the first image.

18. The non-transitory computer-readable storage medium of claim 13, wherein the output routine is to output the link as a visual display to a Picture Arching and Communicating System workstation.

* * * * *